United States Patent [19]
Hastings

[11] Patent Number: 6,148,823
[45] Date of Patent: Nov. 21, 2000

[54] METHOD OF AND SYSTEM FOR CONTROLLING MAGNETIC ELEMENTS IN THE BODY USING A GAPPED TOROID MAGNET

[75] Inventor: Roger N. Hastings, Maple Grove, Minn.

[73] Assignee: Stereotaxis, Inc., St. Louis, Mo.

[21] Appl. No.: 09/271,424

[22] Filed: Mar. 17, 1999

[51] Int. Cl.[7] .................................................. A61B 19/00
[52] U.S. Cl. .......................................... 128/897; 128/898
[58] Field of Search .................................. 128/897–899; 600/9–15, 410, 424

[56] References Cited

U.S. PATENT DOCUMENTS

| | | | |
|---|---|---|---|
| 4,850,963 | 7/1989 | Sparks et al. ............................ | 128/899 |
| 5,592,939 | 1/1997 | Martinelli ................................ | 128/899 |
| 5,788,624 | 8/1998 | Lu et al. .................................... | 600/15 |

*Primary Examiner*—John P. Lacyk
*Attorney, Agent, or Firm*—Bryan K. Wheelock

[57] ABSTRACT

A system for controlling a magnetic element within a selected region of a patient's body includes a magnet assembly comprising first and second mutually attracting, opposed magnet faces separated by a gap; and a magnet support for supporting the magnet assembly adjacent the selected region of the patient's body to apply a magnetic field within the selected region, and moving the gap of the magnet assembly relative to the selected region of the patient's body to change the magnetic field within the selected region. The method A method of controlling a magnetic element within a selected region of a patient's body, the method comprising the controlled application of a magnetic field to the magnetic element in the selected region with a pair of mutually attracting opposed magnets separated by a gap.

28 Claims, 5 Drawing Sheets

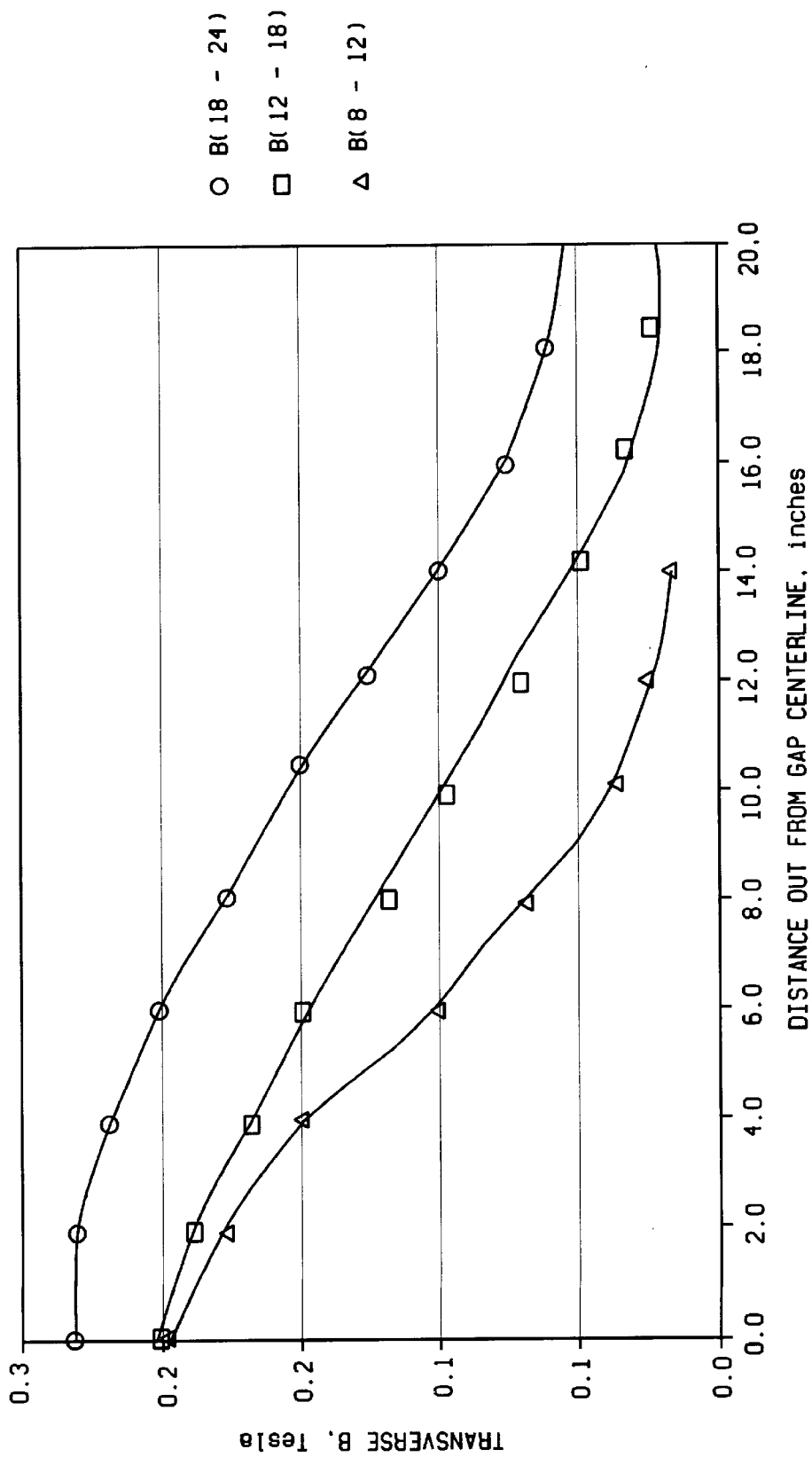

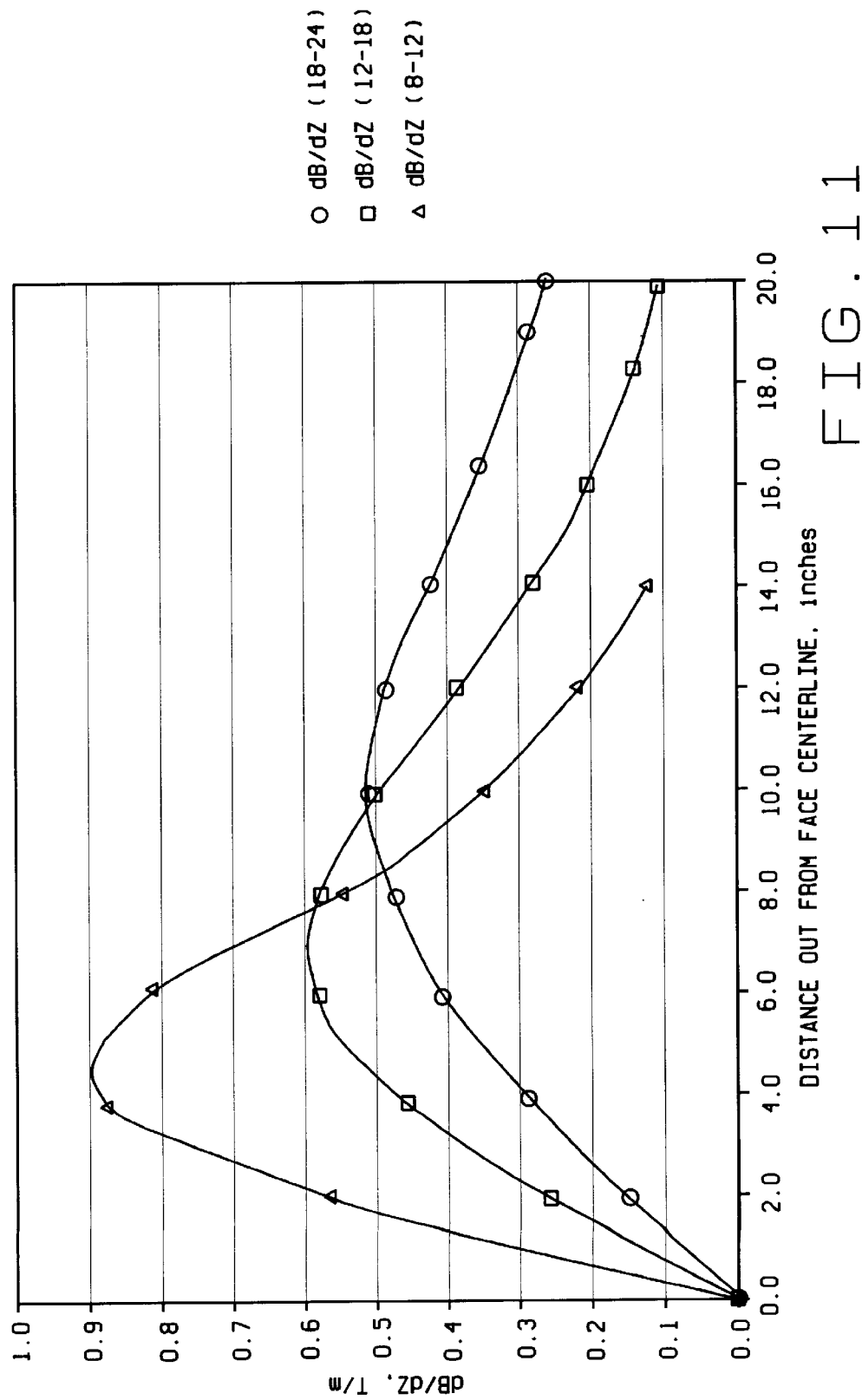

6,148,823

METHOD OF AND SYSTEM FOR CONTROLLING MAGNETIC ELEMENTS IN THE BODY USING A GAPPED TOROID MAGNET

FIELD OF THE INVENTION

This invention relates to a method of, and system for, controlling magnetic elements in the body using a gapped toroid magnet, or its equivalent.

SUMMARY OF THE INVENTION

Magnets have been used for moving magnetic objects in the human body. The earliest use of magnets was more than one hundred years ago to remove shrapnel from wounded soldiers. More recently, magnets have been used in the navigation of medical devices in the human body. A set of stationary superconducting electromagnetic coils can be used to create a variable magnetic field within an operating volume in a patient to orient a medical device in the human body. See, co-pending, co-assigned U.S. patent application Ser. No. 09/211,723, filed Dec. 14, 1998, entitled Open Field System for Magnetic Surgery, incorporated herein by reference. A moveable magnet can also be used to orient and in some cases move a medial device in the human body. See, co-pending, co-assigned U.S. patent application Ser. No. 09/189,633, filed Nov. 10, 1998, entitled Articulated Magnet Guidance System, incorporated herein by reference.

While highly effective, superconducting electromagnet systems are relatively expensive to construct and operate, and thus are not practical for all applications. It can also be difficult to position certain body parts within the set of stationary coils.

Articulating permanent magnets are also highly effective in some applications, but because of limitations on field strength, field direction, and magnetic gradient, they are not practical for all applications.

SUMMARY OF THE INVENTION

The present invention relates to a method of, and system for, controlling magnetic elements in the human body, which employ opposed, attracting magnets separated by a gap. In the preferred embodiment this is implemented with a gapped toroid magnet, which in effect is two opposed attracting magnets connected by a flux return path. This may alternatively be implemented with opposed attracting electromagnetic coils (preferably superconducting electromagnetic coils).

Gapped toroid magnets and their equivalents have a number of desirable properties for controlling magnetic elements within the human body. First, gapped toroid magnets create magnetic fields in and adjacent to the gap that are sufficient for navigating medical devices. The fields created in the gap are relatively uniform, which makes navigation with the fields easier. Furthermore, the gradient in the radial direction is relatively smooth, which also makes navigation easier and safer.

Another useful property of gapped toroid magnets is that field strength increases toward the centerline of the gap, and the gradient peaks at the edge of the gap and thus the gapped toroid magnet can magnetically engage or trap a magnetic element. This allows the gapped toroid magnet to move magnetic elements within the body by translating the magnet relative to the body. This also allows the gapped toroid to concentrate magnetic medical agents, such as therapeutic or diagnostic agents, in a selected region of a patient's body, thus achieving a targeted delivery of such agents. By translating or rotating the gapped toroid magnet, the focusing of such agents in a selected region can be improved.

The system generally comprises a magnet assembly comprising first and second attracting magnets having generally opposed faces separated by a gap. The system further comprises a magnet support for supporting the magnet assembly with the gap adjacent a selected region of a patient's body to apply a magnetic field within the selected region, and moving the gap of the magnet assembly relative to the selected region of the patient's body to change the magnetic field within the selected region. In the preferred embodiment, the magnets are permanent magnets connected by a flux return path. In an alternate embodiment, the magnets are electromagnets, and preferably superconducting electromagnets. In the case of two superconducting coils.

The method generally comprises controlling a magnetic element within a selected region of a patient's body through the controlled application of magnetic fields and/or gradients with a pair of mutually attracting opposed magnets separated by a gap. In the preferred embodiment the magnets are permanent magnets connected by a flux return pathway. In an alternate embodiment the magnets are electromagnets, and preferably superconducting electromagnets.

The magnets can be manipulated to use the field in the gap or adjacent the gap to align a magnetic element, for example a magnetic seed on the distal end of an elongate medical device, for navigation in the body. The magnets can also be manipulated to magnetically engage or trap a magnetic element, for example a magnetic seed on a medical device, and move the seed and its associated medical device by moving the gapped toroid magnet. The magnets can also be used to focus or concentrate the delivery of magnetic medical agents to selected regions of the body. These agents may be either therapeutic or diagnostic agents, and may either be inherently magnetic or associated with a magnetic material, e.g., through microencapsulization or inclusion into a chemical compound containing both therapeutic/diagnostic agents and magnetic means. Because of the unique properties of the magnet configurations, magnetic medical agents will concentrate in the portions of the body in the gap. By moving the magnets it should be possible to further focus the magnetic medical agents to a selected region of the body.

These and other features and advantages will be in part apparent and in part pointed out hereinafter.

BRIEF DESCRIPTION OF THE DRAWINGS

FIG. 10 is a graph of the transverse field versus distance from the centerline between the magnet faces for gap toroids with three different face sizes and gap sizes; and FIG. 11 is a graph of the transverse gradient (perpendicular to the gap direction) for gap toroids with the three face sizes and gap sizes of FIG. 10.

Corresponding reference numerals indicate corresponding parts throughout the several views of the drawings.

DETAILED DESCRIPTION OF THE INVENTION

Figure 1:
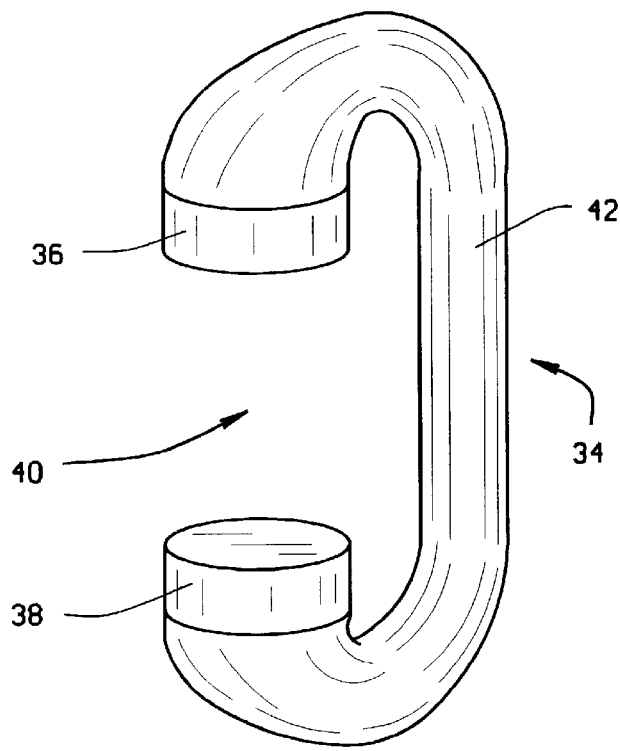
FIG. 1 is a perspective view of a gapped toroid magnet useful in the method and system of the present invention.
Figure 3:
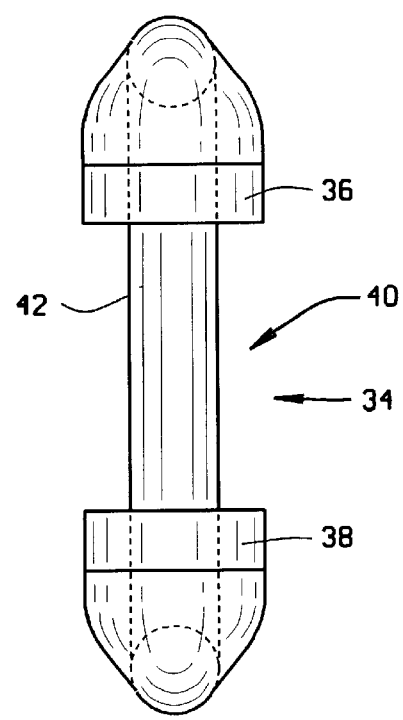
FIG. 3 is a front end elevation view of the gapped toroid magnet.
Figure 2:
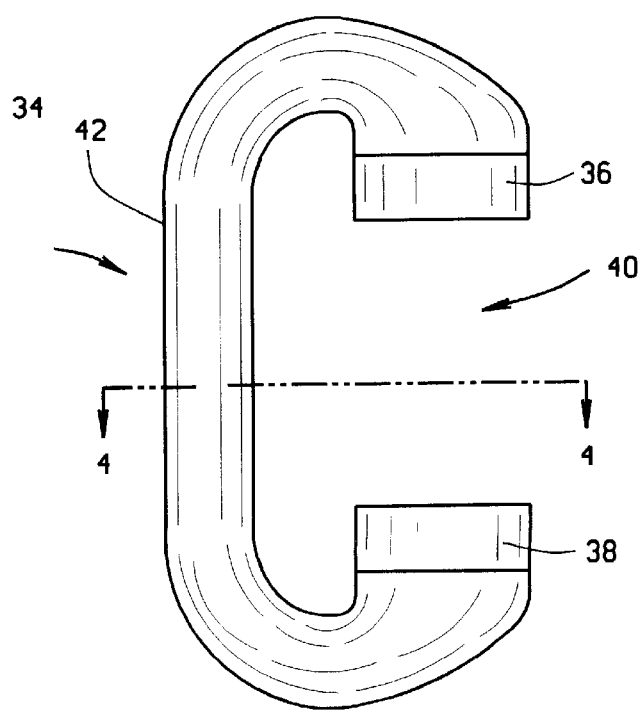
FIG. 2 is a side elevation view of the gapped toroid magnet.
Figure 4:
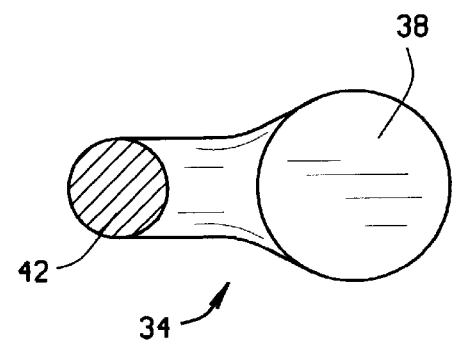
FIG. 4 is a horizontal cross section taken along the plane of line 4—4 in FIG. 3.
Figure 5:
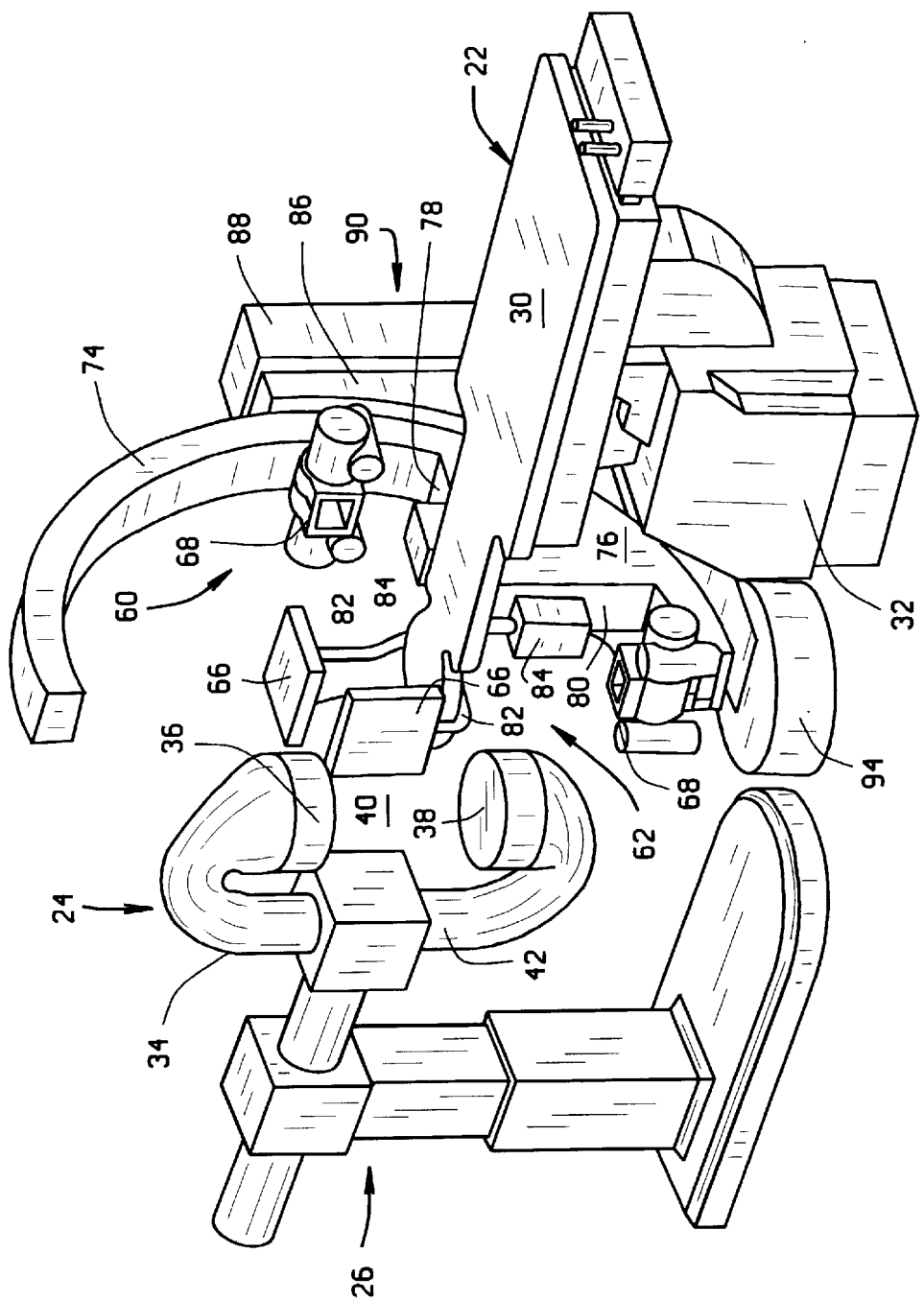
FIG. 5 is a perspective view of a system for controlling a magnetic element in the human body, constructed according to the principles of this invention.
Figure 6:
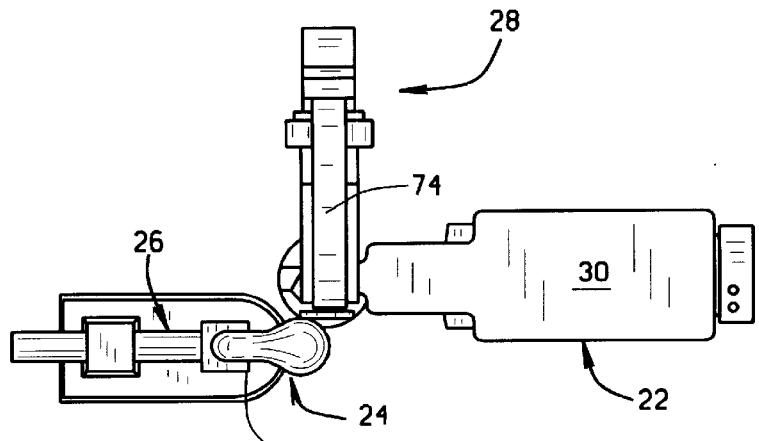
FIG. 6 is a top plan view of the system.
Figure 7:
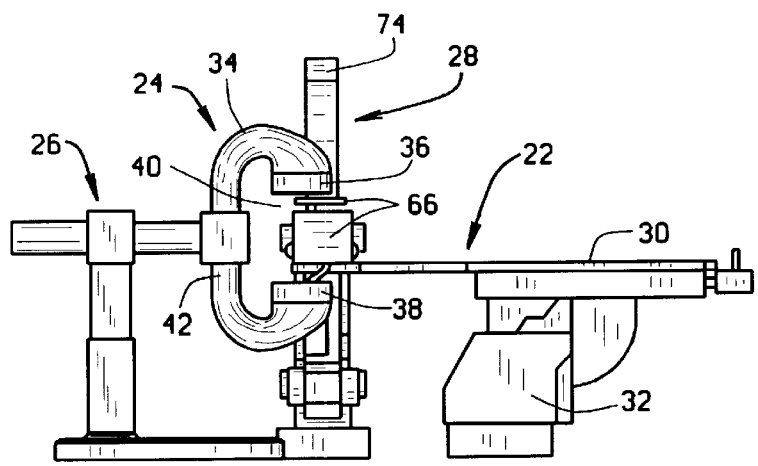
FIG. 7 is a side elevation view of the system.
Figure 8:
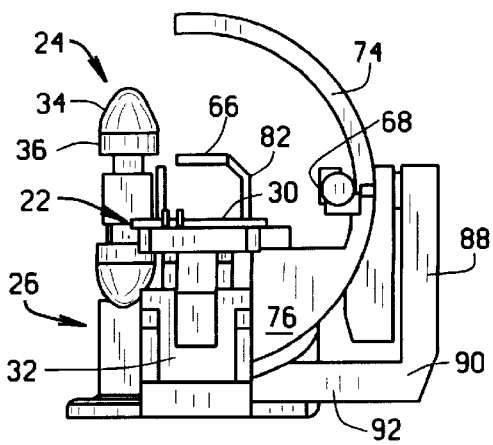
FIG. 8 is a front end elevation view of the system

A system for controlling a magnetic element in the body, constructed according to the principles of the present invention is indicated generally as 20 in FIG. 5. The system 20 comprises a patient support 22, and a magnet assembly 24 on a moveable magnet support 26. The system preferably also includes an imaging assembly 28.

The patient support 22 preferably comprises an elongate bed 30 mounted on a pedestal 32. The foot of bed 30 is oriented toward the front of system and the head of the bed is oriented toward the rear of the system. The bed 30 is preferably movable with respect to the pedestal 32, to allow the patient to be moved relative to the magnet assembly 24. The bed 30 can preferably be moved longitudinally forwardly and rearwardly and vertically upwardly and downwardly, and it can be rotated about its longitudinal axis.

The magnet assembly 24 preferably comprises a gapped toroid magnet 34, which is best shown in FIGS. 1–4. The gapped toroid magnet 34 preferably comprises first and second mutually attracting opposed permanent magnets 36 and 38, separated by a gap 40, and connected by a flux return pathway 42. While the magnet is referred to as a gapped toroid, the magnet need not have an actual toroidal shape. The flux return pathway 42 can have any arbitrary shape, provided that the pathway satisfies magnetic requirements (e.g., does not have overly sharp corners, and is sufficiently large in cross-section that it does not saturate.) as well as structural requirements. The flux return path 42 can be made of a relatively inexpensive permeable magnetic material, such as hiperco, and thus the gapped toroid magnet 34 provides a stronger field for a given permanent magnet cost. The magnets 36 and 38 are preferably made of a permanent magnetic material such as reodymium iron boron (NdFeB) and provide field strengths between them of up to 0.2 Tesla at the center of the gap 40, and up to about 0.5 Tesla adjacent the faces of the magnets. These strengths are sufficient for navigating magnetic elements inside the body. Similar field strengths are achieved adjacent the gap 40, so the gapped toroid magnet 34 can navigate medical devices though body parts that are adjacent to the gap 40 as well as through body parts that are in the gap 40.

The magnetic field across the gap 40 slowly decreases with position, as indicated in the FIG. 10 graph of field strength across the radius of the gap, (taken midway between the magnet faces) for toroid magnets of different face sizes and gap sizes. This relative uniformity makes use of the field in navigation easier. However, as indicated in the FIG. 10 graph, the field strength increases toward the centerline of the gap, which means that magnetic objects will be attracted radially inwardly toward the centerline. This is useful in magnetically engaging magnetic elements to move them with the magnet, and in focusing magnetic medical materials in selected regions of the body.

As indicated in the FIG. 11 graph of gradient across the radius of the gap midway between the magnet faces for toroid magnets of different face sizes and gap sizes, the radial magnetic gradient peaks at the edges of the magnet faces. This means that a magnetic element in the gap 40 between the opposed faces of the magnets 36 and 38 tends to remain in the gap between the faces. Thus a magnetic element can be trapped or magnetically engaged in the gap 40 of the gapped toroid magnet 54 and moved relative to its surroundings simply by moving the gapped toroid magnet. However, even though the radial magnetic gradient peaks at the edge of the of the magnet faces, the peak is not particularly sharp, and the gradient is relatively uniform in the vicinity of the edge, which facilitates ease of use of the gradient in navigation.

The ability to place portions of the body in the gap 40 of the gapped toroid magnet 34 allows larger fields to be applied to the body than is generally possible with a single magnet, and allows the gradient forces to peak within the body instead of always pulling objects to the outside of the body. Thus, as noted above, a magnetic element can be magnetically engaged within the perimeter of the gap, and if this is generally at the midpoint between the magnet faces, there is no additional force on the object tending to push or pull the object out of the body. This permits centering and pulling the objects, instead of simply orienting a magnetic element in the body.

The gap toroid magnet can also be used to focus magnet elements inside the body. Because of the magnetic properties of a gapped toroid magnet, it tends to trap magnetic elements in the gap. This property can be used to concentrate magnetic elements introduced into the body. As described in more detail below, a medical agent (either a therapeutic or diagnostic agent), which is either inherently magnetic or associated with a magnetic material, can be targeted to a selected region in the body by positioning the toroid magnet so that portion of the body containing the selected region is in the gap, and more preferably so that the center of the gap extends through the selected region. The magnet and patient can be moved relative to one another so that the selected region remains in the gap for a greater percentage of the time than the surrounding portions of the body, to further concentrate the medical agent in the selected region.

The gap toroid magnet can be used to establish a magnetic field of a particular direction and strength within an operating region in a patient that is either in the gap or closely adjacent the gap, sufficient to move a magnetic medical device within that portion of a patient inside the operating region. This magnetic medical device may be, for example a magnet-tipped catheter, endoscope, or other elongate medical device or a magnet-tipped guidance for guiding an elongate medical device.

The magnet assembly 24 is preferably mounted on a moveable magnet support 26 so that the gapped toroid magnet 34 can be moved relative to the patient so that a magnetic field can be provided in any direction within the patient to navigate a medical device in the patient. The moveable magnet support 26 also allows the center of the gap 40 to be positioned within the patient's body for concentrating magnetic medical agents. The magnet support 26 permits the magnet to be moved, preferably while keeping the centerline of the gap through the selected region, to maximize the concentration of the magnetic medical agent in the selected region, while minimizing its dispersal in the surrounding tissues also within the gap.

The magnet support 36 can be slidably mounted on tracks to move forwardly and rearwardly (toward and away from the patient support), as well as around the patient. The gapped toroid magnet 34 can be gimballed on the support so that the magnet can be freely oriented with respect to the patient on the patient support to provide the greatest freedom in establishing a magnetic field in a particular direction in a patient and/or for allowing a selected region of the patient's body to be positioned within the gap. Stops can be provided on the tracks to restrict forward motion of the magnet support 26. Of course, some automatic positioning mechanism such as a motorized or servo-controlled mechanism could be provided. This would allow the position of the magnet assembly 34 to be automatically controlled by an external controller or computer.

The imaging assembly 28 comprises at least one imaging device, and in the preferred embodiment two imaging devices 60 and 62, mounted on a C-arm support 70 of C-arm 64. Such supports are made, for example, by General Electric Co. of Syracuse, N.Y. The imaging devices 60 and 62 are preferably arranged perpendicular to each other to provide bi-planar imaging in mutually perpendicular planes. Each of the imaging devices 60 and 62 comprises an imaging plate 66 and an imaging beam source 68. In this preferred embodiment the imaging plates 66 are amorphous silicon imaging plates, known as LAST plates available from Varian, Palo Alto, Calif. These plates 66 are not affected by the presence of magnetic fields, such as those caused by the gapped toroid magnet 34. The imaging beam sources 68 are preferably X-ray sources. Of course some other imaging beam and imaging plate could be used if desired.

As shown in the Figures, C-arm 64 comprises a C-shaped support 74 on which the X-ray sources 68 of the imaging devices 60 and 62 are mounted. The C-shaped support 74 has a wedge shaped block 76 having perpendicular faces 78 and 80 from which arms 82, each mounting one of the imaging plates 66, extend. The arms 82 are hollow, providing a protected path for electrical wiring to the imaging plates 66. The arms 82 are preferably attached to blocks 84 that can move on their respective faces 78 and 80, to permit adjustment of the positions of the imaging plates 66.

The C-shaped support 74 is mounted on body 86, and moves about its circumference relative thereto so that the C-shaped support turns about its central axis. The body 86 is rotably mounted to the vertical leg 88 of a generally L-shaped bracket 90. The body 86 can rotate relative to the L-shaped bracket 90 about a generally horizontal axis. The horizontal leg 92 of the generally L-shaped bracket 86 is pivotally mounted to the base 94 of the system so that the generally L-shaped bracket pivots about a generally vertical axis.

The C-arm 64 thus allows the imaging devices 60 and 62 to be rotated about three mutually perpendicular axes. These axes preferably intersect, and their intersection is preferably in the operating region of the magnet assembly 24. The imaging devices 60 and 62 rotate about a first axis when the C-shaped support 74 turns relative to the body 86. The C-shaped support 74 can preferably rotate clockwise and counter clockwise over a range of about 90°. The imaging devices 60 and 62 rotate about a second generally horizontal axis when the body 86 rotates relative to the L-shaped bracket 90. The body 86 can preferably rotate about 30° forwardly and rearwardly with respect to the L-shaped bracket 90. The imaging devices 60 and 62 rotate about a third generally vertical axis when the L-shaped bracket 90 rotates relative to the base 94. The L-shaped bracket 90 can preferably rotate about 30° forwardly and rearwardly with respect to the base 90.

The imaging apparatus 28 provides bi-planar imaging of the portion of the patient's body. The support arms 82 are configured to clear the patient and the head of the bed, and support the imaging plates 66 and maintaining the imaging plates aligned with their respective imaging beam sources 68. The imaging devices 60 and 62 can be moved around the operating region to accommodate movement of the magnet assembly 24 and to provide the most advantageous views of the operating region so that the surgeon can see the navigation of the magnetic medical device.

Of course some other method of imaging and/or localizing the magnetic element can be used. Stereotactic localization systems using electromagnetic transmitters and receivers, could be used. Ultrasound could also be used for imaging and localizing the magnet elements.

Figure 9:
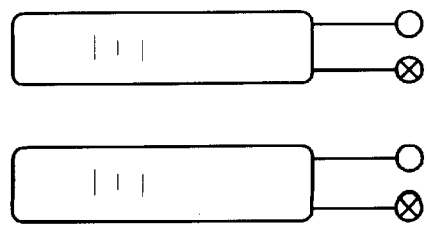
FIG. 9 is a schematic view of two mutually attracting, opposed electromagnets.

Other possible constructions of a gapped toroid magnet useful with the present invention include incorporating a permanent in the return path in addition to, or instead of, the magnets 36 and 38, or incorporating an electromagnet in the return path in addition to, or instead of, the magnets 36 and 38. A generally equivalent magnetic structure to a gapped toroid can be constructed from two mutually attracting, opposed electromagnets, and preferably two superconducting electromagnets as shown schematically in FIG. 9.

Magnetic Navigation

The system 20 of the present invention can be used for magnetic navigation. A magnetic medical device, such as a catheter with a magnetic seed on its distal end is introduced into the patient's body. The physician can visualize the magnetic medical device on the displays for the imaging system 28. The physician determines the appropriate direction to move the medical device and can either manually move the gapped toroid magnet to provide an aligning field in the desired direction, or physician can input the desired direction in a computer controller, which can then substantially move the gapped toroid magnet to provide an aligning field in the desired direction. The medical device can then be advanced by pushing on its proximal end until the next changes in direction, when the gapped toroid magnet can be used to provide an aligning field in the new desired direction. The strongest aligning fields are provided in the gap, but sufficiently strong fields for navigation are provided adjacent the gap, so that it is not essential that the portion of the body through which the magnetic medical device is being navigated fit within the gap.

Magnetic Movement

The system 20 of the present invention can be used to magnetically move magnetic elements in a patient's body. The magnetic element could be a magnetic medical device, such as a catheter with a magnetic seed on its distal end, is introduced into the patient's body. The magnetic seed on the catheter can be magnetically engaged or trapped in the gap 40 of the gapped toroid magnet. Because of the field and gradient properties of the gapped toroid magnet, the magnetic seed tends to remain in the gap 40 even as the gapped toroid magnet is moved. Particularly by actively maintaining the magnetic seed in the middle of the gap (i.e., equidistant between the faces of the magnets) the magnetic seed, and thus its associated medical device, can be moved in any direction perpendicular to the gap direction by moving the magnet in that direction (or by moving the patient in the opposite direction). Particularly where the magnetic element is constrained, for example within a blood vessel or other body lumen, thus can be a safe, fast, and easy way to move a magnetic element within the body.

Magnetic Concentration

The system 20 of the present invention can also be used for the targeted delivery of magnetic agents to selected regions of the body. Again because of the unique properties of the gapped toroid magnet the gapped toroid magnet will tend to magnetically engage or trap magnetic material in the gap. Thus, by introducing a magnetic medical agent, such as a therapeutic or diagnostic agent, into the body, the magnetic medical agent will tend to accumulate in the portions of the body inside the gap of the gapped toroid magnet. The medical agent may be inherently magnetic, or could be microencapsulated with a magnetic substance, or otherwise associated with a magnetic material. Particularly when the magnetic medical agent is introduced in a way that it can freely circulate, e.g., into the blood stream or into the digestive tract, the concentration of the agent in the portions of the body within the gap can be relatively fast. By moving the gapped toroid magnet, either in small translations or rotations, so that the selected region remains in the gap, and particularly in the center of the gap, while the movement of the magnet causes the tissue outside of the selected region to periodically be outside of the gap, the concentrating effect of the gapped toroid magnet can be improved. Thus, by increasing the relative fraction of time the selected region is in the gap because the relative time that the surrounding portions are in the gap, significant concentration could be achieved.

What is claimed is:

1. A method of orienting a magnetic element within a selected region of a patient's body, the method comprising the controlled application of a magnetic field to the magnetic element in the selected region with a pair of mutually attracting opposed magnets separated by a gap.

2. The method according to claim 1, wherein the magnetic field in the selected region is changed by relative movement between the region and the magnets.

3. The method according to claim 2, wherein the pair of opposed magnets are electromagnets.

4. The method according to claim 2, wherein the pair of opposed magnets are permanent magnets connected by a flux return path.

5. A method of orienting a magnetic element within a selected region of a patient's body, the method comprising:
   positioning a magnet assembly comprising two mutually attracting opposed magnets separated by a gap adjacent the selected region of the patient's body; and
   causing relative movement between the selected region and the magnet assembly to selectively change the magnetic field within the selected region in the vicinity of the magnetic element to orient the magnetic element.

6. The method according to claim 5, wherein the opposed magnets are electromagnets.

7. The method according to claim 5, wherein the opposed magnets are permanent magnets connected by a flux return path.

8. The method according to claim 5, wherein the step of positioning a magnet assembly adjacent the selected region comprises positioning the selected region of the patient's body in the gap between the magnets.

9. A method of navigating a magnetic medical device within a selected region of a patient's body, the method comprising:
   introducing an elongate medical device having a magnetically responsive element associated with its distal end in to the patients body;
   applying a magnetic field to the magnetically responsive element with a magnet assembly comprising a pair of mutually attracting opposed magnets separated by a gap to orient the distal end of the elongate medical device; and
   advancing the elongate medical device in the direction of orientation of the distal end.

10. A method of navigating a magnetic element within a selected region of a patient's body, the method comprising:
    introducing the magnetic element into the selected region of the patient's body;
    positioning the selected region of the patient's body in a gap between two mutually attracting opposed magnets, to thereby magnetically engage the magnetic element; and
    causing relative movement between the two opposed magnets and the patient's body to thereby move the magnetic element that is magnetically engaged by the opposed magnets within the selected region of the patient's body.

11. The method according to claim 10 wherein the step of causing relative movement comprises moving the two opposed magnets relative to the patient's body.

12. The method according to claim 10 wherein the step of causing relative movement comprises moving the patient relative to the magnet.

13. A method of targeting the delivery of a medical agent to a selected region of a patient's body comprising:
    introducing a magnetically active medical agent into the patient's body;
    positioning the portion of the patient's body containing the selected region in a gap between two mutually attracting opposed magnets to concentrate the magnetically active medical agent in the portion of the body between the opposed magnets.

14. The method according to claim 13, wherein the medical agent comprises a therapeutic agent.

15. The method according to claim 13, wherein the medical agent comprises a diagnostic agent.

16. The method according to claim 13 wherein the medical agent is not inherently magnetically active, but is associated with a magnetically active substance.

17. The method according to claim 13 further comprising causing relative movement between the patient and the opposed magnets in such a way as to increase the amount of time that the selected region is located within the gap relative to the portions of the body surrounding the selected region.

18. The method according to claim 17 wherein the step of causing relative movement between the patient and the opposed magnets comprises moving the magnets relative to the patient.

19. The method according to claim 18 wherein the step of causing relative movement between the patient and the opposed magnets comprises rotating the magnets about a point in the selected region.

20. The method according to claim 13 wherein the opposed magnets are connected by a flux return path.

21. A method of moving a magnetic element within a selected region of a patient's body, the method comprising the controlled application of a magnetic field to the magnetic element in the selected region with a pair of mutually attracting opposed magnets separated by a gap.

22. The method according to claim 21, wherein the magnetic field in the selected region is changed by relative movement between the region and the magnets.

23. The method according to claim 22, wherein the pair of opposed magnets are electromagnets.

24. The method according to claim 22, wherein the pair of opposed magnets are permanent magnets connected by a flux return path.

25. A method of moving a magnetic element within a selected region of a patient's body, the method comprising:

positioning a magnet assembly comprising two mutually attracting opposed magnets separated by a gap adjacent the selected region of the patient's body; and causing relative movement between the selected region and the magnet assembly to selectively change the magnetic field within the selected region in the vicinity of the magnetic element to move the magnetic element.

26. The method according to claim 25 wherein the opposed magnets are electromagnets.

27. The method according to claim 25 wherein the opposed magnets are permanent magnets connected by a flux return path.

28. The method according to claim 25 wherein the step of positioning a magnet assembly adjacent the selected region comprises positioning the selected region of the patient's body in the gap between the magnets.

* * * * *